United States Patent
Berglund

(10) Patent No.: US 8,052,737 B2
(45) Date of Patent: Nov. 8, 2011

(54) IMPLANTABLE TEMPORARY FLOW RESTRICTOR DEVICE

(75) Inventor: Joseph Berglund, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 240 days.

(21) Appl. No.: 12/435,738

(22) Filed: May 5, 2009

(65) Prior Publication Data

US 2010/0286758 A1    Nov. 11, 2010

(51) Int. Cl.
*A61F 2/82* (2006.01)
(52) U.S. Cl. ........................... 623/1.15; 623/1.44
(58) Field of Classification Search ............... 623/1.15, 623/1.44; *A61F 2/06*
See application file for complete search history.

(56) References Cited

U.S. PATENT DOCUMENTS

| | | | |
|---|---|---|---|
| 4,733,665 | A | 3/1988 | Palmaz |
| 4,800,882 | A | 1/1989 | Gianturco |
| 4,886,062 | A | 12/1989 | Wiktor |
| 5,133,732 | A | 7/1992 | Wiktor |
| 5,292,331 | A | 3/1994 | Boneau |
| 5,421,955 | A | 6/1995 | Lau et al. |
| 5,458,639 | A | 10/1995 | Tsukashima et al. |
| 5,634,946 | A | 6/1997 | Slepian |
| 5,776,161 | A | 7/1998 | Globerman |
| 5,935,162 | A | 8/1999 | Dang |
| 6,090,127 | A | 7/2000 | Globerman |
| 6,113,627 | A | 9/2000 | Jang |
| 6,120,534 | A | 9/2000 | Ruiz |
| 6,267,776 | B1 | 7/2001 | O'Connell |
| 6,500,147 | B2 | 12/2002 | Omaleki et al. |
| 6,554,795 | B2 | 4/2003 | Bagaoisan et al. |
| 6,645,241 | B1 | 11/2003 | Strecker |
| 6,663,661 | B2 | 12/2003 | Boneau |
| 6,730,116 | B1 | 5/2004 | Wolinsky et al. |
| 6,736,827 | B1 | 5/2004 | McAndrew et al. |
| 6,953,476 | B1 | 10/2005 | Shalev |
| 7,147,659 | B2 | 12/2006 | Jones |
| 7,179,250 | B2 | 2/2007 | Heuser |
| 7,264,632 | B2 | 9/2007 | Wright et al. |
| 2006/0041269 | A1 | 2/2006 | Horrigan |
| 2006/0100639 | A1 | 5/2006 | Levin et al. |
| 2007/0055299 | A1* | 3/2007 | Ishimaru et al. ............ 606/191 |

OTHER PUBLICATIONS

Slepian, Marvin J; Hubbell, Jeffrey A; Polymeric endoluminal gel paving: hydrogel systems for local barrier creation and site-specific drug delivery; *Advanced Drug Delivery Reviews* 24(1997) 11-30.

Ostroha, Jamie; Pong, Mona; Lowman, Anthony; Dan, N; Controlling the collapse/swelling transition in charged hydrogels; *Biomaterials 25* (2004) 4345-4353.

* cited by examiner

*Primary Examiner* — Thomas J Sweet
*Assistant Examiner* — Jason-Dennis Stewart

(57) ABSTRACT

An implantable flow restrictor plug is disclosed that is disposed within a deployed endoluminal prosthesis to initially restrict, then gradually restore blood flow through the prosthesis after an angioplasty procedure. Upon initial deployment, the plug has a tubular biodegradable body defining a blood flow lumen therethrough that is sized to effectively reduce the amount of blood flow exiting the prosthesis. An inner surface of the body erodes or biodegrades in vivo to enlarge the plug lumen, thereby gradually restoring blood flow through the prosthesis until blood flow is unimpeded through the prosthesis, i.e., blood flow through the vessel is fully restored. The flow restrictor plug may be attached to the endoluminal prosthesis to be delivered and deployed therewith, or may be formed within a previously deployed prosthesis.

20 Claims, 4 Drawing Sheets

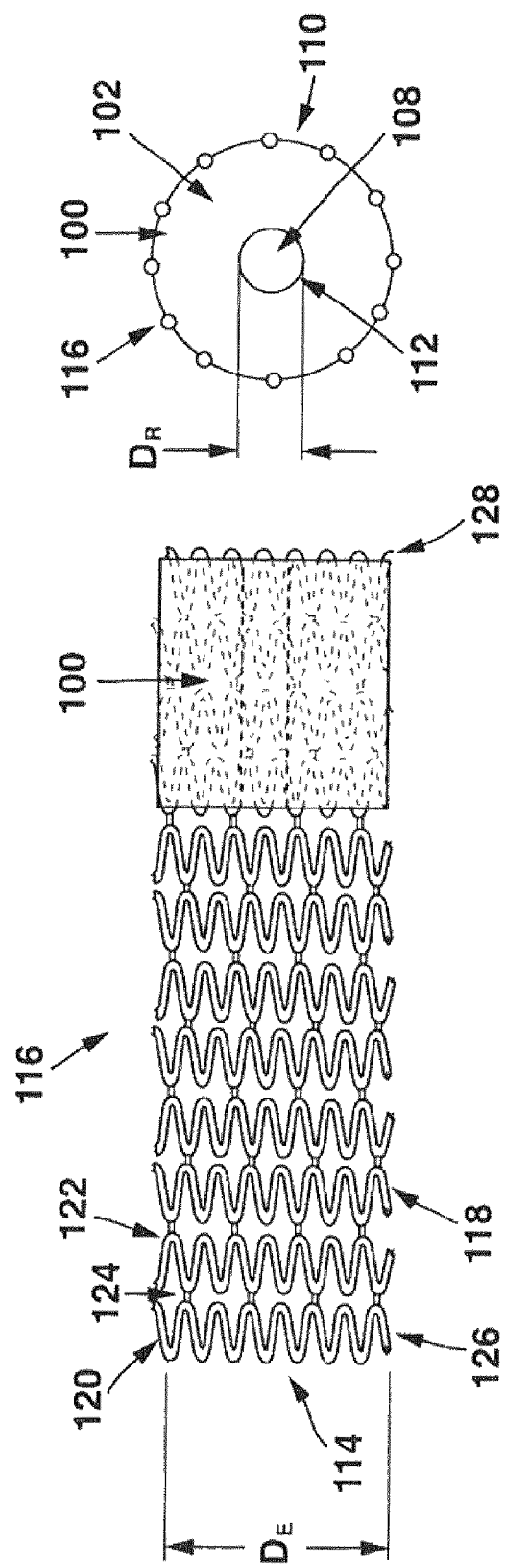

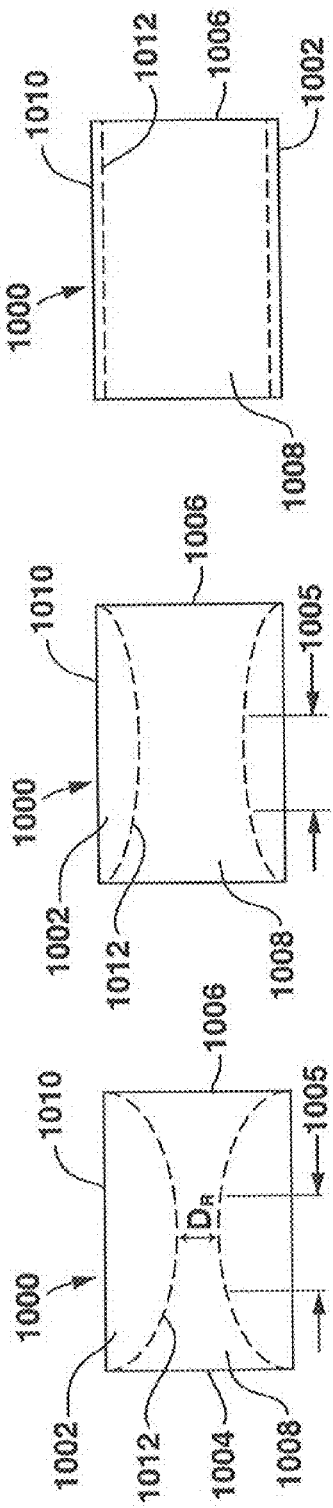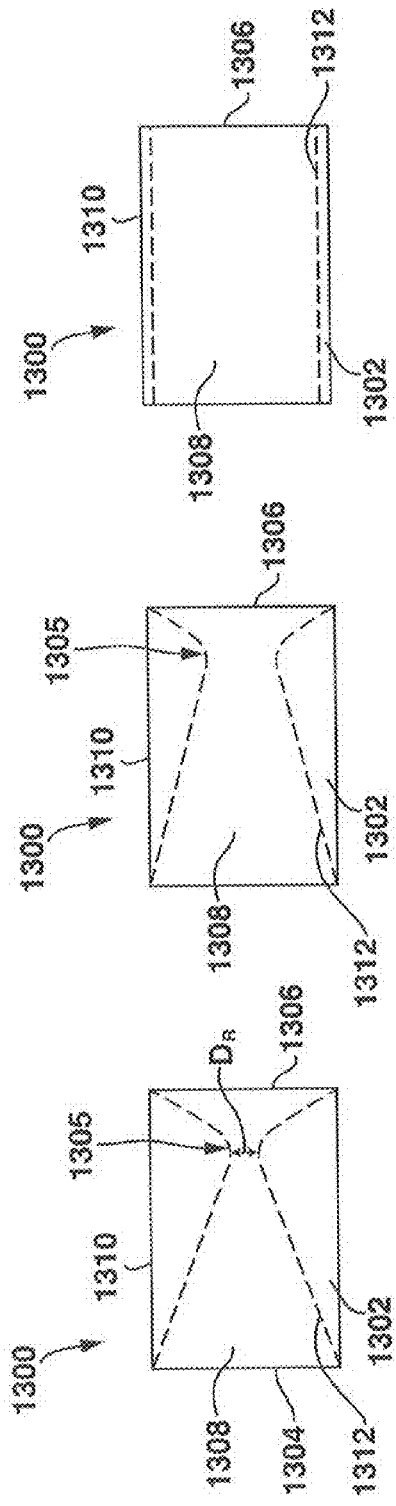

US 8,052,737 B2

IMPLANTABLE TEMPORARY FLOW RESTRICTOR DEVICE

FIELD OF THE INVENTION

The invention is directed to an implantable medical device for initially restricting, then gradually restoring blood flow through a body vessel after an interventional procedure.

BACKGROUND OF THE INVENTION

A wide assortment of endoluminal prostheses have been developed, each providing a uniquely beneficial structure to modify the mechanics of a targeted lumen wall within a body lumen. As used herein, an endoluminal prosthesis is intended to cover a medical device that is adapted for temporary or permanent implantation within a body lumen, including both naturally occurring and artificially made lumens. For example, stent prostheses are known for implantation within body lumens to provide artificial radial support to the wall tissue, which forms the various lumens within the body, and often more specifically, for implantation within the blood vessels of the body. A stent may provide long-term support for damaged or traumatized wall tissues of the lumen or may be implanted, for example, to maintain the patency restored to a blood vessel that was clogged with atherosclerotic plaque. There are numerous conventional applications for stents including cardiovascular, urological, gastrointestinal, and gynecological applications.

Deployment of a stent is accomplished by tracking a catheter through the vascular system of the patient until the stent is located within a target vessel. The treatment site may include target tissue, for example, a lesion which may include plaque obstructing the flow of blood through the target vessel. The stent is expanded or deployed against the vascular wall of the target vessel during or after angioplasty to maintain the opening. Blood flow through the vessel is thereby restored.

However, although relieving a flow constriction in a blood vessel is a primary goal, sudden or abrupt restoration of blood flow may result in reperfusion injury. Reperfusion injury refers to damage to downstream tissue caused when blood supply abruptly returns to the tissue after a period of ischemia. The abrupt restoration of blood flow may shock and overload downstream tissue with high concentrations of oxidative stresses and shear stresses that may cause additional complications such as damage to calcium channels, elevated reactive oxygen species loads, or onset of apoptosis.

Accordingly, a need exists to gradually restore flow and normoxia to ischemic tissue downstream of an obstructive stenosis after an angioplasty procedure. By initially restricting, then gradually restoring blood flow to ischemic tissue, downstream tissue may have time to adapt to the increasing blood flow without incurring reperfusion injury.

BRIEF SUMMARY

An implantable system for initially restricting, then gradually restoring blood flow through a body vessel after an interventional procedure includes a substantially tubular endoluminal prosthesis defining a blood flow lumen therethrough and a biodegradable tubular plug concentrically disposed within the prosthesis lumen. The plug has open ends and an inner surface that defines a blood flow lumen therethrough that is in fluid communication with the prosthesis lumen. The plug lumen has a restrictive diameter that is at least 10% less than an expanded diameter of the prosthesis lumen to reduce blood flow exiting the prosthesis when the plug is in an initially deployed, fully restrictive configuration. The inner surface of the plug erodes in vivo to gradually transform the plug lumen into a final, unrestrictive configuration in which blood flow through the prosthesis lumen is unimpeded by the plug.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a stent prosthesis having a tubular plug extending therein according to an embodiment hereof;

FIG. 2 is an end view of the stent prosthesis and tubular plug of FIG. 1;

FIG. 10 is a side view of a tubular plug according to another embodiment hereof, wherein the flow restrictor device is in an initially deployed, flow restrictive configuration;

FIG. 11 is a side view of the tubular plug of FIG. 10 in a less flow restrictive state after partial dissolution;

FIG. 12 is a side view of the tubular plug of FIG. 10 in an unrestrictive final configuration after substantial dissolution;

FIG. 13 is a side view of a tubular plug according to another embodiment hereof, wherein the flow restrictor device is in an initially deployed, flow restrictive configuration;

FIG. 14 is a side view of the tubular plug of FIG. 13 in a less flow restrictive state after partial dissolution;

FIG. 15 is a side view of the tubular plug of FIG. 13 in an unrestrictive final configuration after substantial dissolution.

DETAILED DESCRIPTION

Figure 3:
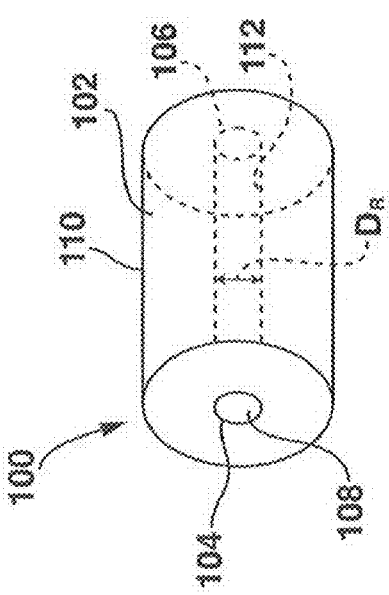
FIG. 3 is a perspective side view of the tubular plug of FIG. 1 in an initially deployed, flow restrictive configuration.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. The terms "biodegradable" and "bioabsorbable" are used in the following description with respect to a property of a material. "Biodegradable" is a material that is capable of being decomposed or broken down in vivo and subsequently excreted. "Bioabsorbable" is a material that is capable of being decomposed or broken down in vivo and subsequently resorbed. Both biodegradable and bioabsorbable materials are suitable for purposes of this application and thus for simplicity, unless otherwise directed, biodegradable materials and bioabsorbable materials will collectively be referred to as "biodegradable" herein. In addition, the terms "resorb", "erode", "dissolve," "dissolution," "biodegrade,"

and "degradation" as used in the following description are intended to refer to the break down of both biodegradable and bioabsorbable materials.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Referring now to FIGS. 1 and 2, embodiments hereof are directed to a flow-restricting tubular plug 100 that may reduce reperfusion injury to tissue downstream of an obstruction in a vessel that has been reopened or removed by an interventional procedure such as angioplasty. Reperfusion injury is expected to be reduced or avoided by restoring blood flow through the vessel gradually rather than abruptly to allow the tissue downstream of a treated obstruction to adapt to the higher shear stresses and oxygen concentrations of the increasing blood flow after an interventional procedure. Once in vivo, tubular plug 100 is concentrically disposed within a blood flow lumen 114 of an expanded or deployed stent 116 and initially restricts or reduces, and then gradually restores, blood flow through the stent. As will be explained in more detail herein, tubular plug 100 may be attached to and delivered in conjunction with stent 116, or may be delivered separately or formed in vivo within deployed stent 116. In one embodiment, tubular plug 100 has a length substantially shorter than the length of stent 116, i.e., between 1 mm and 6 mm, and extends within a distal portion of stent 116 adjacent stent distal end 128. However, as will be understood by those of ordinary skill in the art, plug 100 may alternatively extend within a proximal portion of stent 116 adjacent stent proximal end 126 or be disposed anywhere within stent 116 and may have any suitable length up to the full length of stent 116.

Figure 4:
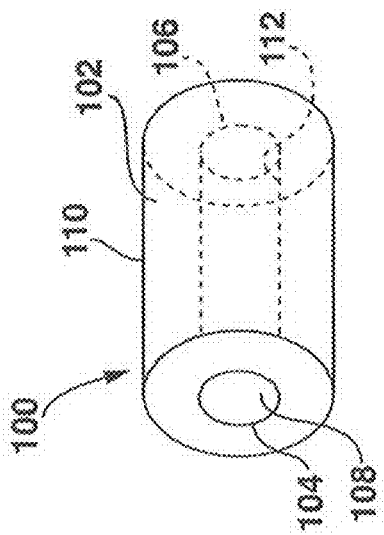
FIG. 4 is a perspective side view of the tubular plug of FIG. 1 in a less flow restrictive state after partial dissolution.
Figure 5:
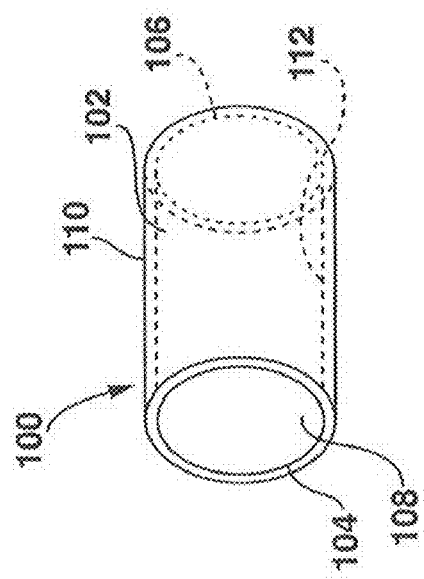
FIG. 5 is a perspective side view of the tubular plug of FIG. 1 in an unrestrictive final configuration after substantial dissolution.

Referring to FIGS. 3-5, flow-restricting tubular plug 100 is shown removed from stent 116 in a perspective side view. In an initially deployed, fully restrictive configuration shown in FIG. 3, tubular plug 100 has a biodegradable body 102 with an outer surface 110 that contacts an inner surface and/or lodges within interstices of deployed stent 116. An inner surface 112 of body 102 defines a blood flow lumen 108 extending between an inlet 104 and an outlet 106. Plug lumen 108 is in fluid communication with prosthesis lumen 114 and in the embodiment of FIGS. 1 and 2 receives blood flow from prosthesis lumen 114. Plug lumen 108 has a restrictive diameter $D_R$ that is at least 10% less than an expanded diameter $D_E$ of prosthesis lumen 114, which is generally equal to a diameter of the vessel lumen in which stent 116 is deployed, to effectively reduce the amount of blood flow exiting stent 116. In an embodiment, the restrictive diameter $D_R$ of plug lumen 108 is between 25% and 75% of an expanded diameter $D_E$ of prosthesis lumen 114. In another embodiment, the restrictive diameter $D_R$ of plug lumen 108 is between 40% and 60% of an expanded diameter $D_E$ of prosthesis lumen 114. As initially deployed, plug lumen 108 is cylindrical with restrictive diameter $D_R$ being substantially constant along the length of plug 100. In an embodiment in which tubular plug 100 is positioned within the proximal inflow portion of deployed stent 116, plug lumen 108 receives blood flow directly from the vessel, and has a restrictive diameter $D_R$ that is at least 10% less than a diameter of the vessel lumen, which is generally equal to expanded diameter $D_E$ of prosthesis lumen 114, to effectively reduce the amount of blood flow entering and passing through stent 116.

In an embodiment, the initially deployed restrictive configuration of plug 100 reduces blood flow exiting stent 116 by 10-90%, i.e., produces a blood flow area blockage of 10-90%. In another embodiment, the initially deployed configuration of plug 100 reduces blood flow exiting stent 116 by 50-75%, i.e., produces a blood flow area blockage of 50-75%. It will be understood by those of ordinary skill in the art that the desired amount of initial blood flow restriction offered by tubular plug 100 may be selected to depend upon the amount of blood flow restriction caused by the pre-existing stenosis. Upon initial deployment of the tubular plug, it is desirable to allow only a slightly higher or greater amount of blood flow through the treated vessel than the amount of blood flow previously allowed by the stenosis. For example, an artery that is judged to have a 90% stenosis may be treated with angioplasty and stenting to restore the lumen to a normal diameter. A tubular plug 100 having an initial 80% flow area blockage may be placed within the stent during or after stent implantation.

Body 102 of tubular plug 100 is formed from a bioabsorbable/biodegradable material that dissolves or breaks down within a vessel. Suitable materials are based on the following list of synthetic and naturally derived polymers and co-polymers, as well as blends, composites, and combinations thereof. Examples of suitable materials that may be adapted for use in embodiments hereof include but are not limited to polylactide [poly-L-lactide (PLLA), poly-DL-lactide (PDLLA)], polyglycolide, polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly (alpha-hydroxy acid) or two or more polymerizable monomers such as trimethylene carbonate, $\epsilon$-caprolactone, polyethylene glycol, 4-tert-butyl caprolactone, N-acetyl caprolactone, poly(ethylene glycol)bis(carboxymethyl) ether, polylactic acid, polyglycolic acid, or polycaprolactone, fibrin, chitosan, or polysaccharides.

Inner surface 112 of body 102 erodes or biodegrades in vivo to gradually transform or enlarge plug lumen 108, thereby gradually restoring blood flow through stent 116. Degradation of plug body 102 may not necessarily occur due to surface erosion but may occur as the structural integrity of plug 102 is impaired and less able to withstand the hemodynamic forces of the blood flow resulting in a gradual increase in the restrictive diameter of plug lumen 108 as plug 102 degrades. Enlargement of plug lumen 108 preferably occurs in a gradual manner to allow the tissue downstream of a treated obstruction to adapt to the increasing blood flow after an interventional procedure. As inner surface 112 dissolves, the restrictive diameter $D_R$ of plug lumen 108 increases to "open" plug lumen 108 to a partially enlarged state as shown in FIG. 4, which permits increased blood flow through plug outlet 106. It will be understood by those of ordinary skill in the art that although inner surface 112 is shown as a smooth surface in FIGS. 4 and 5 for illustrative purposes, erosion of the plug material during dissolution of body 102 may occur in an uneven manner, resulting in a varying or unequal diameter of plug lumen 108 along the length of tubular plug 100. In addition, the surfaces surrounding inlet and outlet 104, 106 of plug body 102 may also experience erosion. Body 102 continues to dissolve until flow through prosthesis lumen 114 of stent 116 is unimpeded, i.e., flow through stent 116 is no longer restricted by tubular plug 100, which is shown in the final unrestricted state of FIG. 5. Blood flow through the vessel is thereby fully restored. It will be understood by those of ordinary skill in the art that, subsequent to plug lumen 108 reaching a fully enlarged state that no longer restricts flow through stent 116, body 102 may completely dissolve, leaving only stent 116 implanted within the target vessel. In one embodiment, tubular plug 100 dissolves to the final state to fully restore blood flow through stent 116 in a period of between one hour and one year. In yet another embodiment, such dissolution to the final state occurs in a period of between six hours and one month. And in yet another embodiment, such dissolution occurs in a period of between six hours and four days.

In one embodiment, the time required for tubular plug 100 to dissolve in vivo to the unrestrictive final state may be selected by utilizing different biodegradable materials having differing rates of in vivo degradation. Each type of biodegradable material has a characteristic degradation rate in the body. Some materials are relatively fast-biodegrading materials (days to weeks) while others are relatively slow-biodegrading materials (months to years). For example, assuming a thickness between approximately 150 µm and 250 µm, polycaprolactone (PCL) fully resorbs within five years, poly-L-lactide (PLLA) fully resorbs within two to five years, poly-DL-lactide (PDLLA) fully resorbs within two to four years, polyglycolic acid (PGA) fully resorbs within one year, poly(lactide-co-glycolide) (PLGA) 85/15 fully resorbs within six to twelve months, and PLGA 50/50 fully resorbs within one to four months. "Fully resorbed" as used herein refers to the time required for complete loss of mass. Some materials, such as polyanhydrides, fully resorb at a very fast rate (hours to days). It is believed that hours to days is a sufficient time period to gradually restore flow in a manner that reduces or avoids reperfusion injury, although longer time periods may be employed.

In yet another embodiment, the time required for tubular plug 100 to dissolve in vivo to the unrestrictive final state may be selected by controlling specific material properties of the biodegradable material of tubular plug 100. For example, molecular weights of the material may be manipulated in order to vary the degradation rate of the material. Generally a material having a higher molecular weight will require a longer time to fully resorb than the same material with a lower molecular weight. In addition, the orientation of the material may be manipulated in order to control the degradation rate of the plug material. Generally a material having a higher degree of crystallinity will require a longer time to fully resorb than the same material with a less-dense crystallization.

Stent 116 is a self-expanding or balloon-expandable substantially tubular prosthesis having a proximal end 126 and a distal end 128. For purposes of this disclosure, stent 116 may be disposed in a blood vessel such that blood flow passes through stent 116 from proximal end 126 to distal end 128, and enters tubular plug 100 at inlet 104. Stent 116 may have a generally cylindrical hollow body formed by a plurality of adjacent connected stent members 118. One of ordinary skill in the art will appreciate that stent 116 can have any number of stent members 118 depending upon the desired length of stent 116. Each stent member 118 is a wavelike or sinusoidal annular band or ring having a pattern of straight segments 120 and crowns 122 connecting adjacent straight segments 120. For purposes of this application, it will be understood that crowns are the concave turns or curves of a wavelike or sinusoidal band. Connections 124 between adjacent stent members 118 are formed where crowns of adjacent stent members 118 are aligned. Connections 124 may be formed by welding or soldering the crowns together, by the addition of a connecting element between the crowns, or by another mechanical method. Further, stent 116 may be formed of pre-connected elements as a unitary structure, such as by laser cutting or etching the entire stent body from a hollow tube or sheet, or may be formed by other wire forming methods as would be understood by those of ordinary skill in the art.

It will be appreciated by one of ordinary skill in the art that stent 116 of FIG. 1 is merely an exemplary stent and that either self-expanding or balloon-expandable stents of various forms can be used in accordance with various embodiments of the present invention. Stent 116 may have any stent configuration or design known in the art. Some examples of stent configurations that are suitable for use in embodiments of the present invention are shown in U.S. Pat. No. 4,733,665 to Palmaz, U.S. Pat. No. 4,800,882 to Gianturco, U.S. Pat. No. 4,886,062 to Wiktor, U.S. Pat. No. 5,133,732 to Wiktor, U.S. Pat. No. 5,292,331 to Boneau, U.S. Pat. No. 5,421,955 to Lau, U.S. Pat. No. 5,776,161 to Globerman, U.S. Pat. No. 5,935,162 to Dang, U.S. Pat. No. 6,090,127 to Globerman, U.S. Pat. No. 6,113,627 to Jang, U.S. Pat. No. 6,663,661 to Boneau, and U.S. Pat. No. 6,730,116 to Wolinsky et al., each of which is incorporated by reference herein in its entirety.

Figure 6:
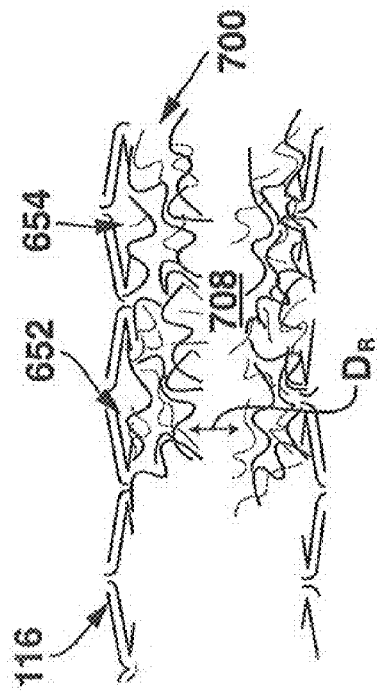
FIGS. 6-9 are partial schematic views of a stent prosthesis having a tubular plug extending therein according to another embodiment hereof.

An alternate embodiment of a flow-restricting tubular plug 700 attached to stent 116 is illustrated in FIGS. 6-9. As shown in FIG. 6, in an unhydrated delivery configuration, a plug layer 650 of hydrophilic material is attached to stent 116 within blood flow lumen 114. In embodiments hereof, the hydrophilic material may be applied via spraying or dip coating to fully embed the stent framework from which plug layer 650 is to extend and then the hydrophilic material may be built up to a desired thickness therefrom. A primer, such as parylene, may be applied to improve the adhesion of plug layer 650 to stent 116. In another embodiment in which stent 116 is of a metallic structure, a chemisorption process, similar to creation of self-assembled monolayers or SAMs, may be used to attach plug layer 650 to the metallic surface of the stent 116. Plug layer 650 includes two components, a first component including a crosslinked hydrogel polymer matrix 652 and a second component including soluble oligomers 654 of low molecular weight (for e.g., having a molecular weight less than 3,000 grams/mole, or alternatively, having a molecular weight less than 6,000 grams/mole). The hydrophilic material of plug layer 650 is selected to have an appropriate rate of swelling that allows time, i.e., between 5-20 minutes, for delivery thereof to the treatment site. In addition, the degree of crosslinking of polymer matrix 652 of plug layer 650 may also be manipulated to affect the rate of swelling. Suitable exemplary materials for plug layer 650 include but are not limited to polyethylene glycol, poly(2-hydroxyethyl methacrylate) (polyHEMA), polyvinyl alcohol or other hydrogel that may be selected for the degree of swelling the material undergoes in vivo.

Figure 7:
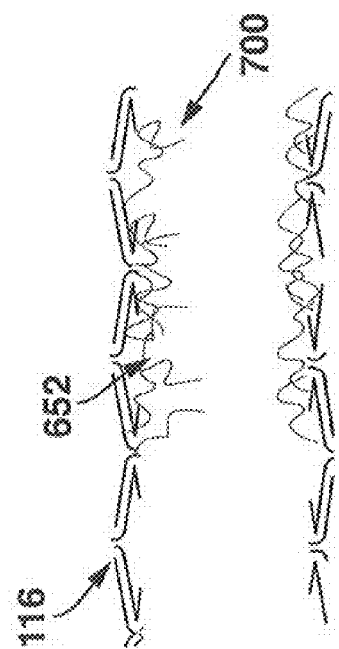
Figure 8:
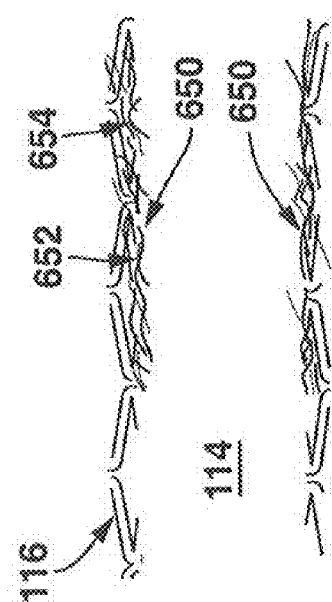
Figure 9:
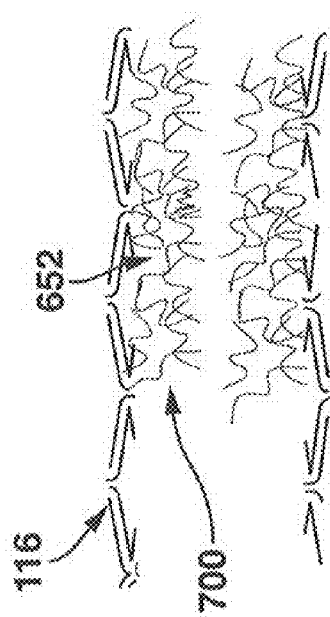

Stent 116 having plug layer 650 attached thereto is collapsed to an insertion diameter, either by crimping onto a balloon catheter or by being contained within a sheath component of a delivery catheter, and is inserted into the vasculature on the delivery system (not shown in FIGS. 6-9 for clarity). Stent 116 is tracked through the vasculature and deployed, by self-expansion or by radial expansion force from a delivery catheter, to its desired diameter at the treatment site. Once stent 116 is deployed, the hydrophilic material of plug layer 650 absorbs water and swells to form in vivo a flow-restricting tubular plug 700 with a blood flow lumen 708 having a restrictive diameter $D_R$ as shown in FIG. 7. The degree of crosslinking of polymer matrix 652 of plug layer 650 may be manipulated to control the final swollen dimensions of tubular plug 700. The balloon catheter or delivery catheter is then retracted and withdrawn from the patient, leaving tubular plug 700 in vivo to temporarily reduce blood flow through stent 116. Shortly after deployment (i.e., 30 minutes to 3 days), low molecular weight soluble oligomers 654 of plug 700 dissolve into the bloodstream, as shown in FIG. 8, resulting in a decreased stiffness of plug 700. With blood flow through plug lumen 708 imparting a shear stress on the defining surface or wall thereof, the less stiff plug 700 deforms, resulting in plug lumen 708 having a larger or increased restrictive diameter $D_R$. Next, degradation of polymer chains within the crosslinked hydrogel polymer matrix 652 of tubular plug 700 occurs in a time period between 3 days and 30 days, leading to a breakdown of the material forming tubular plug 700 to yield a nearly final configuration that will fully restore blood flow through stent 116, as illustrated in FIG. 9.

In embodiments hereof the degree of swelling of polymer matrix 652 and electrostatic driving forces for swelling polymer matrix 652 as a function of crosslink density (average subchain length), as well as salt concentration, and pH may be manipulated as described in "Controlling the Collapse/Swelling Transition in Charged Hydrogels," J. Ostroha et al., (Biomaterials) Volume 25, (2004), Pages 4345-4353, which is incorporated by reference herein in its entirety.

If stent 116 is self-expanding, the delivery system may include an inner shaft having the stent and attached hydrophilic layer mounted at a distal end thereof, and a retractable outer sheath that covers and constrains the stent in a reduced diameter while the delivery system is tracked through a vessel to the treatment site. For example, the delivery system may be the system described in U.S. Pat. No. 7,264,632 to Wright et al., which is hereby incorporated by reference in its entirety, or other such similar delivery systems that are well known in the art. If the stent is balloon-expandable, the stent and attached hydrophilic layer is mounted over an inflatable balloon. Conventional balloon catheters such as those shown or described in U.S. Pat. Nos. 6,736,827; 6,554,795; 6,500,147; and 5,458,639, which are incorporated by reference herein in their entirety, may be used in such a balloon-expandable embodiment.

A flow-restricting tubular plug 1000 for use within blood flow lumen 114 of stent 116 according to another embodiment of the present invention is shown in FIGS. 10-12. Similar to the embodiment of FIGS. 3-5, upon initial deployment, tubular plug 1000 has a cylindrical biodegradable body 1002 with an outer surface 1010 that lodges within deployed stent 116 and is shown in FIG. 10 in a fully restrictive configuration. However, rather than having a cylindrical lumen extending through the plug body 1002, tubular plug 1000 has an hourglass-shaped lumen 1008 extending between an inlet 1004 and an outlet 1006. More particularly, hourglass-shaped lumen 1008 has a first diameter at inlet 1004, a restrictive diameter $D_R$ along a constricted midsection 1005, and a second diameter at outlet 1006. The first and second diameters at inlet 1004 and outlet 1006, respectively, are greater than the restrictive diameter $D_R$ along constricted midsection 1005 and may be approximately equal to each other, as well as substantially equal to an expanded diameter $D_E$ of stent lumen 114. The restrictive diameter $D_R$ of constricted midsection 1005 effectively reduces the amount of blood flow exiting stent 116. As inner surface 1012 gradually dissolves over time in vivo, the diameter of constricted midsection 1005 increases to open plug lumen 1008 to a partially enlarged state that allows increased blood flow through the plug outlet 1006 as shown in FIG. 11. Body 1002 continues to dissolve until blood flow through deployed stent 116 is unimpeded, i.e., flow through the deployed stent is no longer restricted by tubular plug 1000, which is shown in its final, unrestrictive state in FIG. 12.

A flow-restricting tubular plug 1300 for use within blood flow lumen 114 of stent 116 according to another embodiment of the present invention is shown in FIGS. 13-15. Similar to the above embodiments, upon initial deployment, tubular plug 1300 has a cylindrical biodegradable body 1302 with an outer surface 1310 that lodges within deployed stent 116 and is illustrated in FIG. 13 in a fully restrictive configuration. In this embodiment, tubular plug 1300 has a tapered or conical lumen 1308 extending between an inlet 1304 and an outlet 1306. More particularly, conical lumen 1308 has a first diameter at inlet 1304 that tapers to a restrictive diameter $D_R$ at a constriction 1305. In addition, conical lumen 1308 may have a flared or second diameter at outlet 1306. The first and second diameters at inlet 1304 and outlet 1306, respectively, are greater than the restrictive diameter $D_R$ at constriction 1305 and may be approximately equal to each other, as well as be substantially equal to the expanded diameter $D_E$ of stent lumen 114. The restrictive diameter $D_R$ of constriction 1305 effectively reduces the amount of blood flow exiting stent 116. The hourglass-shape of lumen 1008 or the nozzle-like shape of lumen 1308 may improve the hydrodynamics of blood flow, viz. hemodynamics through tubular plugs 1000, 1300 to maintain laminar flow, reducing eddy currents and their sequelae, such as thrombus formation. As inner surface 1312 gradually dissolves over time in vivo, the diameter of constriction 1305 increases or opens to a partially enlarged state to allow increased blood flow through outlet 1306 of tubular plug 1300 as shown in FIG. 14. Body 1302 continues to dissolve until blood flow through deployed stent 116 is unimpeded, i.e., flow through the deployed stent is no longer restricted by tubular plug 1300, which is shown in its final unrestrictive state in FIG. 15.

In accordance with embodiments hereof, flow-restricting tubular plugs 100, 1000, 1300 may be formed in vivo within a previously deployed stent 116. In such an embodiment, a delivery catheter having a balloon at the distal end thereof is tracked through the vasculature until the balloon is positioned within deployed stent 116. The balloon may expand to have a conventional, tubular profile or a profile resembling an hourglass, dumbbell, or other suitable shape for forming tubular plugs in accordance with embodiments hereof, such as tubular plugs 100, 1000, 1300. The delivery catheter includes a lumen for delivering a plug material into the isolated space formed between an outside surface of the balloon and stent 116. A viscous material for forming tubular plugs 100, 1000, 1300 is then injected through the delivery catheter into the space between the balloon and deployed stent 116. The plug material coagulates, cures, sets or hardens in vivo to form flow-restricting tubular plugs 100, 1000, 1300. In embodiments hereof, curing may be activated by light, water or heat and may be set or hardened in vivo in between 5 seconds and 15 minutes depending on the plug material and the method of curing. The balloon is then deflated and withdrawn from within the tubular plug and removed from the patient.

In an embodiment, the plug material may be a biodegradable hydrogel such as those described in "Polymeric endoluminal gel paving: hydrogel systems for local barrier creation and site-specific drug delivery," Marvin J. Slepian and Jeffrey A. Hubbell (Advanced Drug Delivery Reviews) Volume 24, Issue 1, 15 Feb. 1997, Pages 11-30, which is incorporated by reference herein in its entirety. More particularly, photopolymerizable hydrogels are disclosed including polyalkylene oxides, such as block copolymers of polyethylene oxide (PEO aka PEG) and polypropylene oxide (PPO), that are modified with biodegradable moieties and capped with photopolymerizable acrylate end groups that may be adapted for use as a biodegradable hydrogel in accordance with embodiments hereof. In another embodiment, the plug material is a fibrin or fibrin-containing material such that blood would naturally activate fibrinolysis and erode tubular plugs 100, 1000, 1300. The delivery catheter is then retracted and withdrawn from the patient, leaving tubular plugs 100, 1000, 1300 in vivo to temporarily reduce blood flow through stent 116. A balloon catheter as shown and described in U.S. Patent Application Pub. 2006/0041269 to Horrigan, herein incorporated by reference in its entirety, may be adapted for use in embodiments hereof.

In another embodiment where a flow-restricting tubular plug in accordance with embodiments hereof may be formed in vivo within deployed stent 116, a delivery catheter having a conventional or other shaped balloon at the distal end thereof is tracked through the vasculature until the balloon is positioned within deployed stent 116. A relatively thick, moldable gel material for forming tubular plug 100 is delivered via injection through the delivery catheter, and inflation of the balloon embeds the gel material against the interior surface of deployed stent 116 to form tubular plugs 100, 1000, 1300. The gel material is fluid enough to be directed through a catheter but is in a moldable state immediately after being inserted into the vessel. Alternatively, the gel material may be delivered as a coating on the balloon, and inflation of the balloon embeds the gel material into deployed stent 116 to form tubular plugs 100, 1000, 1300. In one embodiment, the gel material is a dextran or other material having long polysaccharide chains. The delivery catheter is then retracted and withdrawn from the patient, leaving tubular plugs 100, 1000, 1300 in vivo to temporarily reduce blood flow through stent 116. A dual balloon catheter as shown and described in U.S. Pat. No. 7,179,250 to Heuser, herein incorporated by reference in its entirety, may be adapted for use in forming tubular plugs in vivo in accordance with embodiments hereof.

Connections between or attachment of flow-restricting plugs and stents in accordance with embodiments hereof may be improved by increasing contact area between the plug and stent, such as by selecting stents with a geometry or shape that has multiple contact areas/points with the plug, and/or by altering the chemistry at the plug/stent interface, such as with the application of a suitable primer. As well other means of providing a strong attachment between the plug and stent may be utilized as would be known to one of ordinary skill in the art.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A system for gradually restoring blood flow through vessel, the system comprising:
    a substantially tubular endoluminal prosthesis of a metallic material defining a blood flow lumen therethrough; and
    a biodegradable tubular plug concentrically disposed within the prosthesis lumen, the plug having an inner surface that defines a blood flow lumen therethrough that is in fluid communication with the prosthesis lumen, wherein the plug lumen has a restrictive diameter that is at least 10% less than an expanded diameter of the prosthesis lumen to reduce blood flow exiting the prosthesis when the plug is in an initially deployed, fully restrictive configuration and wherein the inner surface of the plug is adapted to erode in vivo to gradually transform the plug lumen into a final, unrestrictive configuration in which blood flow through the prosthesis lumen is unimpeded by the plug.

2. The system of claim 1, wherein the plug lumen is cylindrical and the restrictive diameter is constant along a length of the plug in the initially deployed, fully restrictive configuration.

3. The system of claim 1, wherein the plug lumen has an hourglass shape such that the restrictive diameter is along a constricted midsection of the plug lumen.

4. The system of claim 1, wherein the plug lumen has a conical shape with a first diameter that tapers to the restrictive diameter, wherein the first diameter of the plug lumen is substantially equal to the expanded diameter of the prosthesis lumen.

5. The system of claim 1, wherein the plug has a length that is less than that of the prosthesis and is disposed within a distal portion of the prosthesis.

6. The system of claim 1, wherein the plug is of a hydrophilic material and in a delivery configuration forms an unhydrated layer of hydrophilic material on an inner surface of the prosthesis.

7. The system of claim 1, wherein the restrictive diameter is between 25%-75% of the expanded diameter of the prosthesis lumen.

8. The system of claim 7, wherein the restrictive diameter is between 40%-60% of the expanded diameter of the prosthesis lumen.

9. The system of claim 1, wherein the inner surface of the plug is adapted to erode to the final, unrestrictive configuration in a time period between one hour and one year.

10. The system of claim 9, wherein the inner surface of the plug is adapted to erode to the final, unrestrictive configuration in a time period between six hours and four days.

11. A method of gradually restoring blood flow through a vessel, the method comprising the steps of:
    deploying a substantially tubular endoluminal prosthesis of a metallic material defining a blood flow lumen therethrough at a treatment site within the vessel; and
    disposing a biodegradable tubular plug within the lumen of the deployed prosthesis, the plug having an inner surface that defines a blood flow lumen therethrough that is in fluid communication with the prosthesis lumen, wherein the plug lumen has a restrictive diameter that is at least 10% less than an expanded diameter of the prosthesis lumen to reduce blood flow exiting the prosthesis when the plug is in an initially deployed, fully restrictive configuration and wherein the inner surface of the plug erodes in vivo to gradually transform the plug lumen into a final, unrestrictive configuration in which blood flow through the prosthesis lumen is unimpeded by the plug.

12. The method of claim 11, wherein the plug lumen is cylindrical and the restrictive diameter is constant along a length of the plug in the initially deployed, fully restrictive configuration.

13. The method of claim 11, wherein the plug lumen has an hourglass shape such that the restrictive diameter is along a constricted midsection of the plug lumen.

14. The method of claim 11, wherein the plug lumen has a conical shape with a first diameter that tapers to the restrictive diameter, wherein the first diameter of the plug lumen is substantially equal to the expanded diameter of the prosthesis lumen.

15. The method of claim 11, wherein the plug has a length substantially shorter than that of the deployed endoluminal prosthesis and is implanted within a distal portion of the deployed endoluminal prosthesis.

16. The method of claim 11, wherein the restrictive diameter is between 25%-75% of an expanded diameter of the prosthesis lumen.

17. The method of claim 16, wherein the restrictive diameter is between 40%-60% of an expanded diameter of the prosthesis lumen.

18. The method of claim 11, wherein the inner surface of the plug erodes to the final, unrestrictive configuration in a time period between one hour and one year.

19. The method of claim 18, wherein the inner surface of the plug erodes to the final, unrestrictive configuration in a time period between six hours and four days.

20. The method of claim 11, wherein the step of disposing the plug within the endoluminal prosthesis includes forming the plug from a viscous material that is delivered between an outer surface of a balloon of a delivery catheter and an inner surface of the prosthesis.

* * * * *